United States Patent
Dunn et al.

(10) Patent No.: US 11,293,908 B2
(45) Date of Patent: *Apr. 5, 2022

(54) SYSTEM AND METHOD FOR DETECTING GAS RECIRCULATION OR AIRWAY OCCLUSION

(71) Applicant: Manufacturing Resources International, Inc., Alpharetta, GA (US)

(72) Inventors: William Dunn, Alpharetta, GA (US); John Schuch, Buford, GA (US)

(73) Assignee: Manufacturing Resources International, Inc., Alpharetta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/984,739

(22) Filed: Aug. 4, 2020

(65) Prior Publication Data

US 2020/0378939 A1    Dec. 3, 2020

Related U.S. Application Data

(63) Continuation of application No. 16/440,531, filed on Jun. 13, 2019, now Pat. No. 10,782,276.
(Continued)

(51) Int. Cl.
*G01N 33/00*    (2006.01)
*H05K 7/20*    (2006.01)
*G08B 17/10*    (2006.01)

(52) U.S. Cl.
CPC ......... *G01N 33/0063* (2013.01); *G08B 17/10* (2013.01); *H05K 7/20972* (2013.01)

(58) Field of Classification Search
CPC . G01N 33/0063; G08B 17/10; H05K 7/20972
See application file for complete search history.

(56) References Cited

U.S. PATENT DOCUMENTS

| 4,093,355 A | 6/1978 | Kaplit et al. |
| 4,593,978 A | 6/1986 | Mourey et al. |

(Continued)

FOREIGN PATENT DOCUMENTS

| AU | 2010218083 B2 | 10/2016 |
| AU | 2016203550 B2 | 3/2018 |

(Continued)

OTHER PUBLICATIONS

Novitsky, T. et al., Design How-To, Driving LEDs versus CCFLs for LCD backlighting, EE Times, Nov. 12, 2007, 6 pages, AspenCore.
(Continued)

*Primary Examiner* — Hongmin Fan
(74) *Attorney, Agent, or Firm* — Standley Law Group LLP; Jeffrey S. Standley; Adam J. Smith

(57) ABSTRACT

A display assembly which detects abnormal operating conditions, such as gas recirculation or airway occlusion, is provided. An electronic display is located within a housing. An airflow pathway travels through the housing and is configured to accept, circulate, and exhaust air by way of one or more fans. One or more sensors measure characteristics of the air. Weather conditions for a location of the display assembly are gathered, measurements from the sensors are received, and a determination is made as to whether the measurements of the ingested air are within a margin of error expected measurements derived from the gathered weather conditions. An alert is generated if the measurements of the ingested air are not within the margin of error.

19 Claims, 7 Drawing Sheets

Related U.S. Application Data

(60) Provisional application No. 62/684,996, filed on Jun. 14, 2018.

(56) References Cited

U.S. PATENT DOCUMENTS

| | | | |
|---|---|---|---|
| 4,634,225 A | 1/1987 | Hairn et al. |
| 5,029,982 A | 7/1991 | Nash |
| 5,086,314 A | 2/1992 | Aoki et al. |
| 5,088,806 A | 2/1992 | McCartney et al. |
| 5,162,785 A | 11/1992 | Fagard |
| 5,247,374 A | 9/1993 | Terada |
| 5,285,677 A | 2/1994 | Oehler |
| 5,559,614 A | 9/1996 | Urbish et al. |
| 5,661,374 A | 8/1997 | Cassidy et al. |
| 5,748,269 A | 5/1998 | Harris et al. |
| 5,767,489 A | 6/1998 | Ferrier |
| 5,783,909 A | 7/1998 | Hochstein |
| 5,786,801 A | 7/1998 | Ichise |
| 5,808,418 A | 9/1998 | Pitman et al. |
| 5,818,010 A | 10/1998 | McCann |
| 5,952,992 A | 9/1999 | Helms |
| 5,991,153 A | 11/1999 | Heady et al. |
| 6,085,152 A | 7/2000 | Doerfel |
| 6,089,751 A | 7/2000 | Conover et al. |
| 6,144,359 A | 11/2000 | Grave |
| 6,153,985 A | 11/2000 | Grossman |
| 6,157,143 A | 12/2000 | Bigio et al. |
| 6,157,432 A | 12/2000 | Helbing |
| 6,181,070 B1 | 1/2001 | Dunn et al. |
| 6,191,839 B1 | 2/2001 | Briley et al. |
| 6,259,492 B1 | 7/2001 | Imoto et al. |
| 6,292,228 B1 | 9/2001 | Cho |
| 6,297,859 B1 | 10/2001 | George |
| 6,380,853 B1 | 4/2002 | Long |
| 6,388,388 B1 | 5/2002 | Weindorf et al. |
| 6,400,101 B1 | 6/2002 | Biebl et al. |
| 6,417,900 B1 | 7/2002 | Shin et al. |
| 6,496,236 B1 | 12/2002 | Cole et al. |
| 6,509,911 B1 | 1/2003 | Shimotono |
| 6,535,266 B1 | 3/2003 | Nemeth et al. |
| 6,556,258 B1 | 4/2003 | Yoshida et al. |
| 6,628,355 B1 | 9/2003 | Takahara |
| 6,701,143 B1 | 3/2004 | Dukach et al. |
| 6,712,046 B2 | 3/2004 | Nakamichi |
| 6,753,661 B2 | 6/2004 | Muthu et al. |
| 6,753,842 B1 | 6/2004 | Williams et al. |
| 6,762,741 B2 | 7/2004 | Weindorf |
| 6,798,341 B1 | 9/2004 | Eckel et al. |
| 6,809,718 B2 | 10/2004 | Wei et al. |
| 6,812,851 B1 | 11/2004 | Dukach et al. |
| 6,813,375 B2 | 11/2004 | Armato III et al. |
| 6,839,104 B2 | 1/2005 | Taniguchi et al. |
| 6,850,209 B2 | 2/2005 | Mankins et al. |
| 6,885,412 B2 | 4/2005 | Ohnishi et al. |
| 6,886,942 B2 | 5/2005 | Okada et al. |
| 6,891,135 B2 | 5/2005 | Pala et al. |
| 6,943,768 B2 | 9/2005 | Cavanaugh et al. |
| 6,982,686 B2 | 1/2006 | Miyachi et al. |
| 6,996,460 B1 | 2/2006 | Krahnstoever et al. |
| 7,015,470 B2 | 3/2006 | Faytlin et al. |
| 7,038,186 B2 | 5/2006 | De Brabander et al. |
| 7,064,733 B2 | 6/2006 | Cok et al. |
| 7,083,285 B2 | 8/2006 | Hsu et al. |
| 7,136,076 B2 | 11/2006 | Evanicky et al. |
| 7,174,029 B2 | 2/2007 | Agostinelli et al. |
| 7,176,640 B2 | 2/2007 | Tagawa |
| 7,236,154 B1 | 6/2007 | Kerr et al. |
| 7,307,614 B2 | 12/2007 | Vinn |
| 7,324,080 B1 | 1/2008 | Hu et al. |
| 7,330,002 B2 | 2/2008 | Joung |
| 7,354,159 B2 | 4/2008 | Nakamura et al. |
| 7,447,018 B2 | 11/2008 | Lee et al. |
| 7,474,294 B2 | 1/2009 | Leo et al. |
| 7,480,042 B1 | 1/2009 | Phillips et al. |
| 7,518,600 B2 | 4/2009 | Lee |
| 7,595,785 B2 | 9/2009 | Jang |
| 7,639,220 B2 | 12/2009 | Yoshida et al. |
| 7,659,676 B2 | 2/2010 | Hwang |
| 7,692,621 B2 | 4/2010 | Song |
| 7,724,247 B2 | 5/2010 | Yamazaki et al. |
| 7,795,574 B2 | 9/2010 | Kennedy et al. |
| 7,795,821 B2 | 9/2010 | Jun |
| 7,800,706 B2 | 9/2010 | Kim et al. |
| 7,804,477 B2 | 9/2010 | Sawada et al. |
| 7,982,706 B2 | 7/2011 | Ichikawa et al. |
| 8,087,787 B2 | 1/2012 | Medin |
| 8,111,371 B2 | 2/2012 | Suminoe et al. |
| 8,125,163 B2 | 2/2012 | Dunn et al. |
| 8,144,110 B2 | 3/2012 | Huang |
| 8,175,841 B2 | 5/2012 | Ooghe |
| 8,194,031 B2 | 6/2012 | Yao et al. |
| 8,248,203 B2 | 8/2012 | Hanwright et al. |
| 8,325,057 B2 | 12/2012 | Salter |
| 8,352,758 B2 | 1/2013 | Atkins et al. |
| 8,508,155 B2 | 8/2013 | Schuch |
| 8,569,910 B2 | 10/2013 | Dunn et al. |
| 8,605,121 B2 | 12/2013 | Chu et al. |
| 8,700,226 B2 | 4/2014 | Schuch et al. |
| 8,797,372 B2 | 8/2014 | Liu |
| 8,810,501 B2 | 8/2014 | Budzelaar et al. |
| 8,823,630 B2 | 9/2014 | Roberts et al. |
| 8,829,815 B2 | 9/2014 | Dunn et al. |
| 8,895,836 B2 | 11/2014 | Amin et al. |
| 8,901,825 B2 | 12/2014 | Reed |
| 8,982,013 B2 | 3/2015 | Sako et al. |
| 8,983,385 B2 | 3/2015 | Macholz |
| 8,988,011 B2 | 3/2015 | Dunn |
| 9,030,129 B2 | 5/2015 | Dunn et al. |
| 9,167,655 B2 | 10/2015 | Dunn et al. |
| 9,286,020 B2 | 3/2016 | Dunn et al. |
| 9,400,192 B1 | 7/2016 | Salser, Jr. et al. |
| 9,448,569 B2 | 9/2016 | Schuch et al. |
| 9,451,060 B1 | 9/2016 | Bowers et al. |
| 9,516,485 B1 | 12/2016 | Bowers et al. |
| 9,536,325 B2 | 1/2017 | Bray et al. |
| 9,622,392 B1 | 4/2017 | Bowers et al. |
| 9,799,306 B2 | 10/2017 | Dunn et al. |
| 9,867,253 B2 | 1/2018 | Dunn et al. |
| 9,881,528 B2 | 1/2018 | Dunn |
| 9,924,583 B2 | 3/2018 | Schuch et al. |
| 10,255,884 B2 | 4/2019 | Dunn et al. |
| 10,321,549 B2 | 6/2019 | Schuch et al. |
| 10,409,544 B2 | 9/2019 | Park et al. |
| 10,412,816 B2 | 9/2019 | Schuch et al. |
| 10,440,790 B2 | 10/2019 | Dunn et al. |
| 10,578,658 B2 | 3/2020 | Dunn et al. |
| 10,586,508 B2 | 3/2020 | Dunn |
| 10,593,255 B2 | 3/2020 | Schuch et al. |
| 10,607,520 B2 | 3/2020 | Schuch et al. |
| 2002/0009978 A1 | 1/2002 | Dukach et al. |
| 2002/0020090 A1 | 2/2002 | Sanders |
| 2002/0050974 A1 | 5/2002 | Rai et al. |
| 2002/0065046 A1 | 5/2002 | Mankins et al. |
| 2002/0084891 A1 | 7/2002 | Mankins et al. |
| 2002/0101553 A1 | 8/2002 | Enomoto et al. |
| 2002/0112026 A1 | 8/2002 | Fridman et al. |
| 2002/0126248 A1 | 9/2002 | Yoshida |
| 2002/0154138 A1 | 10/2002 | Wada et al. |
| 2002/0164962 A1 | 11/2002 | Mankins et al. |
| 2002/0167637 A1 | 11/2002 | Burke et al. |
| 2002/0190972 A1 | 12/2002 | Ven de Van |
| 2003/0007109 A1 | 1/2003 | Park |
| 2003/0088832 A1 | 5/2003 | Agostinelli et al. |
| 2003/0122810 A1 | 7/2003 | Tsirkel et al. |
| 2003/0204342 A1 | 10/2003 | Law et al. |
| 2003/0214242 A1 | 11/2003 | Berg-johansen |
| 2003/0230991 A1 | 12/2003 | Muthu et al. |
| 2004/0032382 A1 | 2/2004 | Cok et al. |
| 2004/0036622 A1 | 2/2004 | Dukach et al. |
| 2004/0036697 A1 | 2/2004 | Kim et al. |
| 2004/0036834 A1 | 2/2004 | Ohnishi et al. |
| 2004/0113044 A1 | 6/2004 | Ishiguchi |
| 2004/0165139 A1 | 8/2004 | Anderson et al. |
| 2004/0201547 A1 | 10/2004 | Takayama |

(56) References Cited

U.S. PATENT DOCUMENTS

| | | |
|---|---|---|
| 2004/0243940 A1 | 12/2004 | Lee et al. |
| 2005/0012734 A1 | 1/2005 | Johnson et al. |
| 2005/0024538 A1 | 2/2005 | Park et al. |
| 2005/0043907 A1 | 2/2005 | Eckel et al. |
| 2005/0049729 A1 | 3/2005 | Culbert et al. |
| 2005/0073518 A1 | 4/2005 | Bontempi |
| 2005/0094391 A1 | 5/2005 | Campbell et al. |
| 2005/0127796 A1 | 6/2005 | Olesen et al. |
| 2005/0140640 A1 | 6/2005 | Oh et al. |
| 2005/0184983 A1 | 8/2005 | Brabander et al. |
| 2005/0231457 A1 | 10/2005 | Yamamoto et al. |
| 2005/0242741 A1 | 11/2005 | Shiota et al. |
| 2006/0007107 A1 | 1/2006 | Ferguson |
| 2006/0022616 A1 | 2/2006 | Furukawa et al. |
| 2006/0038511 A1 | 2/2006 | Tagawa |
| 2006/0049533 A1 | 3/2006 | Kamoshita |
| 2006/0087521 A1 | 4/2006 | Chu et al. |
| 2006/0125773 A1 | 6/2006 | Ichikawa et al. |
| 2006/0130501 A1 | 6/2006 | Singh et al. |
| 2006/0197474 A1 | 9/2006 | Olsen |
| 2006/0197735 A1 | 9/2006 | Vuong et al. |
| 2006/0214904 A1 | 9/2006 | Kimura et al. |
| 2006/0215044 A1 | 9/2006 | Masuda et al. |
| 2006/0220571 A1 | 10/2006 | Howell et al. |
| 2006/0238531 A1 | 10/2006 | Wang |
| 2006/0244702 A1 | 11/2006 | Yamazaki et al. |
| 2007/0013828 A1 | 1/2007 | Cho et al. |
| 2007/0047808 A1 | 3/2007 | Choe et al. |
| 2007/0152949 A1 | 7/2007 | Sakai |
| 2007/0171647 A1 | 7/2007 | Artwohl et al. |
| 2007/0173297 A1 | 7/2007 | Cho et al. |
| 2007/0200513 A1 | 8/2007 | Ha et al. |
| 2007/0222730 A1 | 9/2007 | Kao et al. |
| 2007/0230167 A1 | 10/2007 | McMahon et al. |
| 2007/0242153 A1 | 10/2007 | Tang et al. |
| 2007/0247594 A1 | 10/2007 | Tanaka |
| 2007/0268234 A1 | 11/2007 | Wakabayashi et al. |
| 2007/0268241 A1 | 11/2007 | Nitta et al. |
| 2007/0273624 A1 | 11/2007 | Geelen |
| 2007/0279369 A1 | 12/2007 | Yao et al. |
| 2007/0291198 A1 | 12/2007 | Shen |
| 2007/0297163 A1 | 12/2007 | Kim et al. |
| 2007/0297172 A1 | 12/2007 | Furukawa et al. |
| 2008/0019147 A1 | 1/2008 | Erchak et al. |
| 2008/0055297 A1 | 3/2008 | Park |
| 2008/0074382 A1 | 3/2008 | Lee et al. |
| 2008/0078921 A1 | 4/2008 | Yang et al. |
| 2008/0084166 A1 | 4/2008 | Tsai |
| 2008/0111958 A1 | 5/2008 | Kleverman et al. |
| 2008/0136770 A1 | 6/2008 | Peker et al. |
| 2008/0143187 A1 | 6/2008 | Hoekstra et al. |
| 2008/0151082 A1 | 6/2008 | Chan |
| 2008/0165203 A1 | 7/2008 | Pantfoerder |
| 2008/0170031 A1 | 7/2008 | Kuo |
| 2008/0176345 A1 | 7/2008 | Yu et al. |
| 2008/0185976 A1 | 8/2008 | Dickey et al. |
| 2008/0204375 A1 | 8/2008 | Shin et al. |
| 2008/0218501 A1 | 9/2008 | Diamond |
| 2008/0224892 A1 | 9/2008 | Bogolea et al. |
| 2008/0246871 A1 | 10/2008 | Kupper et al. |
| 2008/0266554 A1 | 10/2008 | Sekine et al. |
| 2008/0278099 A1 | 11/2008 | Bergfors et al. |
| 2008/0278100 A1 | 11/2008 | Hwang |
| 2008/0303918 A1 | 12/2008 | Keithley |
| 2009/0009997 A1 | 1/2009 | Sanfilippo et al. |
| 2009/0033612 A1 | 2/2009 | Roberts et al. |
| 2009/0079416 A1 | 3/2009 | Vinden et al. |
| 2009/0085859 A1 | 4/2009 | Song |
| 2009/0091634 A1 | 4/2009 | Kennedy et al. |
| 2009/0104989 A1 | 4/2009 | Williams et al. |
| 2009/0109129 A1 | 4/2009 | Cheong et al. |
| 2009/0135167 A1 | 5/2009 | Sakai et al. |
| 2009/0152445 A1 | 6/2009 | Gardner, Jr. |
| 2009/0278766 A1 | 11/2009 | Sako et al. |
| 2009/0284457 A1 | 11/2009 | Botzas et al. |
| 2009/0289968 A1 | 11/2009 | Yoshida |
| 2010/0033413 A1 | 2/2010 | Song et al. |
| 2010/0039366 A1 | 2/2010 | Hardy |
| 2010/0039414 A1 | 2/2010 | Bell |
| 2010/0039440 A1 | 2/2010 | Tanaka et al. |
| 2010/0060861 A1 | 3/2010 | Medin |
| 2010/0066484 A1 | 3/2010 | Hanwright et al. |
| 2010/0177750 A1 | 7/2010 | Essinger et al. |
| 2010/0194725 A1 | 8/2010 | Yoshida et al. |
| 2010/0231602 A1 | 9/2010 | Huang |
| 2010/0253660 A1 | 10/2010 | Hashimoto |
| 2011/0032285 A1 | 2/2011 | Yao et al. |
| 2011/0032489 A1 | 2/2011 | Kimoto et al. |
| 2011/0050738 A1 | 3/2011 | Fujioka et al. |
| 2011/0058326 A1 | 3/2011 | Idems et al. |
| 2011/0074737 A1 | 3/2011 | Hsieh et al. |
| 2011/0074803 A1 | 3/2011 | Kerofsky |
| 2011/0102630 A1 | 5/2011 | Rukes |
| 2011/0148904 A1 | 6/2011 | Kotani |
| 2011/0163691 A1 | 7/2011 | Dunn |
| 2011/0175872 A1 | 7/2011 | Chuang et al. |
| 2011/0193872 A1 | 8/2011 | Biernath et al. |
| 2011/0231676 A1 | 9/2011 | Atkins et al. |
| 2011/0260534 A1 | 10/2011 | Rozman et al. |
| 2011/0279426 A1 | 11/2011 | Imamura et al. |
| 2011/0283199 A1 | 11/2011 | Schuch et al. |
| 2012/0075362 A1 | 3/2012 | Ichioka et al. |
| 2012/0081279 A1 | 4/2012 | Greenebaum et al. |
| 2012/0176420 A1 | 7/2012 | Liu |
| 2012/0182278 A1 | 7/2012 | Ballestad |
| 2012/0212520 A1 | 8/2012 | Matsui et al. |
| 2012/0268436 A1 | 10/2012 | Chang |
| 2012/0269382 A1 | 10/2012 | Kiyohara et al. |
| 2012/0284547 A1 | 11/2012 | Culbert et al. |
| 2013/0027370 A1 | 1/2013 | Dunn et al. |
| 2013/0070567 A1 | 3/2013 | Marzouq |
| 2013/0098425 A1 | 4/2013 | Amin et al. |
| 2013/0113973 A1 | 5/2013 | Miao |
| 2013/0158730 A1 | 6/2013 | Yasuda et al. |
| 2013/0278868 A1 | 10/2013 | Dunn et al. |
| 2013/0344794 A1 | 12/2013 | Shaw et al. |
| 2014/0002747 A1 | 1/2014 | Macholz |
| 2014/0132796 A1 | 5/2014 | Prentice et al. |
| 2014/0139116 A1 | 5/2014 | Reed |
| 2014/0184980 A1 | 7/2014 | Onoue |
| 2014/0190240 A1 | 7/2014 | He et al. |
| 2014/0204452 A1 | 7/2014 | Branson |
| 2014/0232709 A1 | 8/2014 | Dunn et al. |
| 2014/0293605 A1 | 10/2014 | Chemel et al. |
| 2014/0365965 A1 | 12/2014 | Bray et al. |
| 2015/0062892 A1 | 3/2015 | Krames et al. |
| 2015/0070337 A1 | 3/2015 | Bell et al. |
| 2015/0310313 A1 | 10/2015 | Murayama et al. |
| 2015/0319882 A1 | 11/2015 | Dunn et al. |
| 2015/0346525 A1 | 12/2015 | Wolf et al. |
| 2015/0348460 A1 | 12/2015 | Cox et al. |
| 2016/0037606 A1 | 4/2016 | Dunn et al. |
| 2016/0162297 A1 | 6/2016 | Shao |
| 2016/0198545 A1 | 7/2016 | Dunn et al. |
| 2016/0334811 A1 | 11/2016 | Marten |
| 2016/0335698 A1 | 11/2016 | Jones et al. |
| 2016/0338181 A1 | 11/2016 | Schuch et al. |
| 2016/0338182 A1 | 11/2016 | Schuch et al. |
| 2016/0358530 A1 | 12/2016 | Schuch et al. |
| 2016/0358538 A1 | 12/2016 | Schuch et al. |
| 2017/0111486 A1 | 4/2017 | Bowers et al. |
| 2017/0111520 A1 | 4/2017 | Bowers et al. |
| 2017/0168295 A1 | 6/2017 | Iwami |
| 2018/0012565 A1 | 1/2018 | Dunn |
| 2018/0040297 A1 | 2/2018 | Dunn et al. |
| 2018/0042134 A1 | 2/2018 | Dunn et al. |
| 2018/0088368 A1 | 3/2018 | Notoshi et al. |
| 2018/0132327 A1 | 5/2018 | Dunn et al. |
| 2018/0206316 A1 | 7/2018 | Schuch et al. |
| 2019/0021189 A1* | 1/2019 | Kim .............. H05K 7/20181 |
| 2019/0237045 A1 | 8/2019 | Dunn et al. |
| 2019/0339312 A1 | 11/2019 | Dunn et al. |

(56) References Cited

U.S. PATENT DOCUMENTS

| | | |
|---|---|---|
| 2019/0383778 A1 | 12/2019 | Dunn et al. |
| 2020/0150162 A1 | 5/2020 | Dunn et al. |
| 2020/0211505 A1 | 7/2020 | Dunn |

FOREIGN PATENT DOCUMENTS

| | | |
|---|---|---|
| AU | 2016262614 B2 | 1/2019 |
| AU | 2016308187 B2 | 2/2020 |
| CA | 2754371 C | 11/2017 |
| CA | 2849902 C | 2/2019 |
| EP | 0313331 B1 | 2/1994 |
| EP | 1686777 A1 | 8/2006 |
| EP | 2299723 A1 | 3/2011 |
| EP | 2401738 A2 | 1/2012 |
| EP | 2769376 A1 | 8/2014 |
| EP | 2577389 B1 | 5/2017 |
| EP | 3295452 A1 | 3/2018 |
| EP | 2401738 B1 | 5/2018 |
| EP | 3338273 A1 | 6/2018 |
| GB | 2369730 A | 5/2002 |
| JP | 3-153212 A | 7/1991 |
| JP | 5-18767 A | 1/1993 |
| JP | 8193727 A | 7/1996 |
| JP | 8-338981 A | 12/1996 |
| JP | 11-160727 A | 6/1999 |
| JP | 2000122575 A | 4/2000 |
| JP | 2004325629 A | 11/2004 |
| JP | 2005-148490 A | 6/2005 |
| JP | 2005265922 A | 9/2005 |
| JP | 2005-338266 A | 12/2005 |
| JP | 2006-106345 A | 4/2006 |
| JP | 2006-145890 A | 6/2006 |
| JP | 2006318733 A | 11/2006 |
| JP | 2007003638 A | 1/2007 |
| JP | 2007322718 A | 12/2007 |
| JP | 2008-34841 A | 2/2008 |
| JP | 2008-83290 A | 4/2008 |
| JP | 2008122695 A | 5/2008 |
| JP | 2009031622 A | 2/2009 |
| JP | 2010-181487 A | 8/2010 |
| JP | 2010-282109 A | 12/2010 |
| JP | 2011-59543 A | 3/2011 |
| JP | 2018-523148 A | 8/2018 |
| JP | 2018-525650 A | 9/2018 |
| KR | 10-2006-0016469 A | 2/2006 |
| KR | 10-0768584 B1 | 10/2007 |
| KR | 10-2008-0000144 A | 1/2008 |
| KR | 10-2008-0013592 A | 2/2008 |
| KR | 10-2008-0086245 A | 9/2008 |
| KR | 10-2009-0014903 A | 2/2009 |
| KR | 10-2010-0019246 A | 2/2010 |
| KR | 10-2011-0125249 A | 11/2011 |
| KR | 10-2014-0054747 A | 5/2014 |
| KR | 10-1759265 B1 | 7/2017 |
| KR | 10-1931733 B1 | 12/2018 |
| KR | 10-2047433 B1 | 11/2019 |
| KR | 10-2130667 B1 | 6/2020 |
| WO | 2008/050402 A1 | 5/2008 |
| WO | 2010/141739 A2 | 12/2010 |
| WO | 2011/052331 A1 | 5/2011 |
| WO | 2011/130461 A2 | 10/2011 |
| WO | 2011/150078 A2 | 12/2011 |
| WO | 2013/044245 A1 | 3/2013 |
| WO | 2016/183576 A1 | 11/2016 |
| WO | 2017/031237 A1 | 2/2017 |
| WO | 2017/210317 A1 | 12/2017 |
| WO | 2018/009917 A1 | 1/2018 |
| WO | 2019/241546 A1 | 12/2019 |
| WO | 2020/081687 A1 | 4/2020 |

OTHER PUBLICATIONS

Vogler, A. et al., Photochemistry and Beer, Journal of Chemical Education, Jan. 1982, pp. 25-27, vol. 59, No. 1.

Zeeff, T.M. et al., Abstract of EMC analysis of 18" LCD Monitor, Electromagnetic Compatibility, IEEE International Symposium, Aug. 21-25, 2000, vol. 1, 1 page.

Lee, X., What is Gamma Correction in Images and Videos?, http://xahlee.info/img/what_is_gamma_correction.html, Feb. 24, 2010, 4 pages.

Hoober, S. et al., Designing Mobile Interfaces, 2012, pp. 519-521, O'Reilly Media.

Outdoorlink, Inc., SmartLink Website User Manual, http://smartlink.outdoorlinkinc.com/docs/SmartLinkWebsiteUserManual.pdf, 2017, 33 pages.

Outdoorlink, Inc., SmartLink One, One Relay, http://smartlinkcontrol.com/billboard/one-relay/, retrieved Apr. 17, 2019, 2007-16, 6 pages.

Outdoorlink, Inc., SmartLink One Out of Home Media Controller, 2016, 1 page.

Vertigo Digital Displays, Innovation on Display FlexVu Totem Brochure, 2014, 6 pages.

* cited by examiner

SYSTEM AND METHOD FOR DETECTING GAS RECIRCULATION OR AIRWAY OCCLUSION

CROSS-REFERENCE TO RELATED APPLICATION

This application is a continuation of U.S. application Ser. No. 16/440,531 filed Jun. 13, 2019, which claims the benefit of U.S. Provisional Application No. 62/684,996 filed Jun. 14, 2018, the disclosure of each of which are hereby incorporated by reference as if fully restated herein.

TECHNICAL FIELD

Exemplary embodiments of the present invention relate generally to a system and method for detecting gas recirculation or airway occlusion.

BACKGROUND AND SUMMARY OF THE INVENTION

Electronic displays are increasingly being used in both indoor and outdoor applications. Such electronic displays are sometimes placed in assemblies with a ruggedized housing to facilitate use of the electronic display in various indoor or outdoor environments. However, these electronic displays and related equipment generate heat which may need to be removed. To thermally manage the display assemblies, sometimes fans are utilized which move gas through the display assemblies. For example, ambient air may be moved through the housing of the display assembly in an open loop. In exemplary embodiments, circulating gas may also be moved through the display assembly in a closed loop. The circulating gas may be made to thermally interact with the ambient air in the open loop. Fans may be installed at various locations to facilitate the movement of gas though the open and closed loops.

The display assembly may ingest relatively cool, ambient air. The ambient air may be passed through the display assembly where it absorbs the heat within the display assembly. Sometimes, this is accomplished by causing the relatively cool ambient air to thermally interact with relatively warm, heat generating components of the display assembly. Such components may include, but are not limited to, the backlight. Alternatively, or in addition, the display assembly may be thermally managed by causing the ambient air to thermally interact with the closed loop of relatively warm circulating gas. In such cases, the circulating gas in the closed loop may be caused to thermally interact with said heat generating components of the display assembly. Regardless, the now heated ambient air may be exhausted from the display assembly and returned to the ambient environment for cooling. While the ambient environment may comprise ambient air of sufficient temperature to cool the display assembly, the heated, exhaust ambient air may sometimes be re-ingested by the display assembly. This may impact the thermal management capabilities of the display assembly as the re-ingested gas is generally warmer than the rest of the ambient air. Furthermore, the open loop pathways may periodically be occluded by ingested contaminants, debris, or other items, which may impact the thermal management capabilities of the display assembly. Therefore, what is needed is a system and method for detecting gas recirculation or airway occlusion in a display assembly.

These disclosures provide a system and method for detecting gas recirculation or airway occlusion in a display assembly. The location of the display assembly may be determined. Weather data for the location may be gathered by way of a communications network and network interface device. Additionally, data regarding the characteristics of the ingested ambient air may be gathered. This data may be gathered by sensors located on or around the intake for the ambient air and/or at other locations along the open loop pathway. The weather data and the data regarding characteristics of the ingested ambient air may be stored on an electronic storage device. A system control board comprising a processor may compare the weather data to the data regarding the characteristics of the ingested ambient air. If the measured characteristics of the ingested ambient air match the gathered weather data, then the process may be repeated. However, if the measured characteristics of the ingested ambient air do not match the gathered weather data, then an alert may be generated. The alert may indicate re-ingestion of heated exhaust ambient air or an occlusion in the open loop pathway. Occlusions in the closed loop pathway are unlikely to be experienced as the closed loop pathway is generally, but not necessarily, substantially sealed from contaminants and debris which may otherwise be ingested into the open loop pathway. In exemplary embodiments, operation of the display assembly may also be adjusted or a technician may be dispatched to inspect the unit. The speed of the fans and the amount of ambient air ingested may be adjusted to accommodate varying ambient conditions, such as but not limited to, amount of sunlight, time of day, temperature, season, and the like.

The backlight is generally a significant source of heat production in such display assemblies. As such, the power sent to the backlight may additionally or alternatively be adjusted in order to reduce the heat generated by the display assembly.

The process may be repeated continuously or periodically. In exemplary embodiments, a margin of error may be used in the match determination to account for discrepancies which may be accountable to the inherent variation in weather conditions at the location the weather data was gathered at and the location of the display assembly. The margin of error may alternatively or additionally be based on historical information. The margin of error may be larger during sunrise or sunset periods.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

The terminology used herein is for the purpose of describing exemplary embodiments only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, indicate the presence of stated features, integers, steps, operations, elements, and/or components, but do not preclude the presence or addition of one or more other features, integers, steps, operations, elements, components, and/or groups thereof.

Exemplary system and method embodiments are described herein with reference to illustrations that are schematic in nature and, as such, variations from the shapes of the illustrations as a result, for example, of manufacturing techniques and/or tolerances, are to be expected. Thus, embodiments of the inventive concept should not be construed as limited to the particular shapes of regions illustrated herein but are to include deviations in shapes.

Unless otherwise defined, all terms (including technical and scientific terms) used herein have the same meaning as commonly understood by one of ordinary skill in the art to which the inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1:
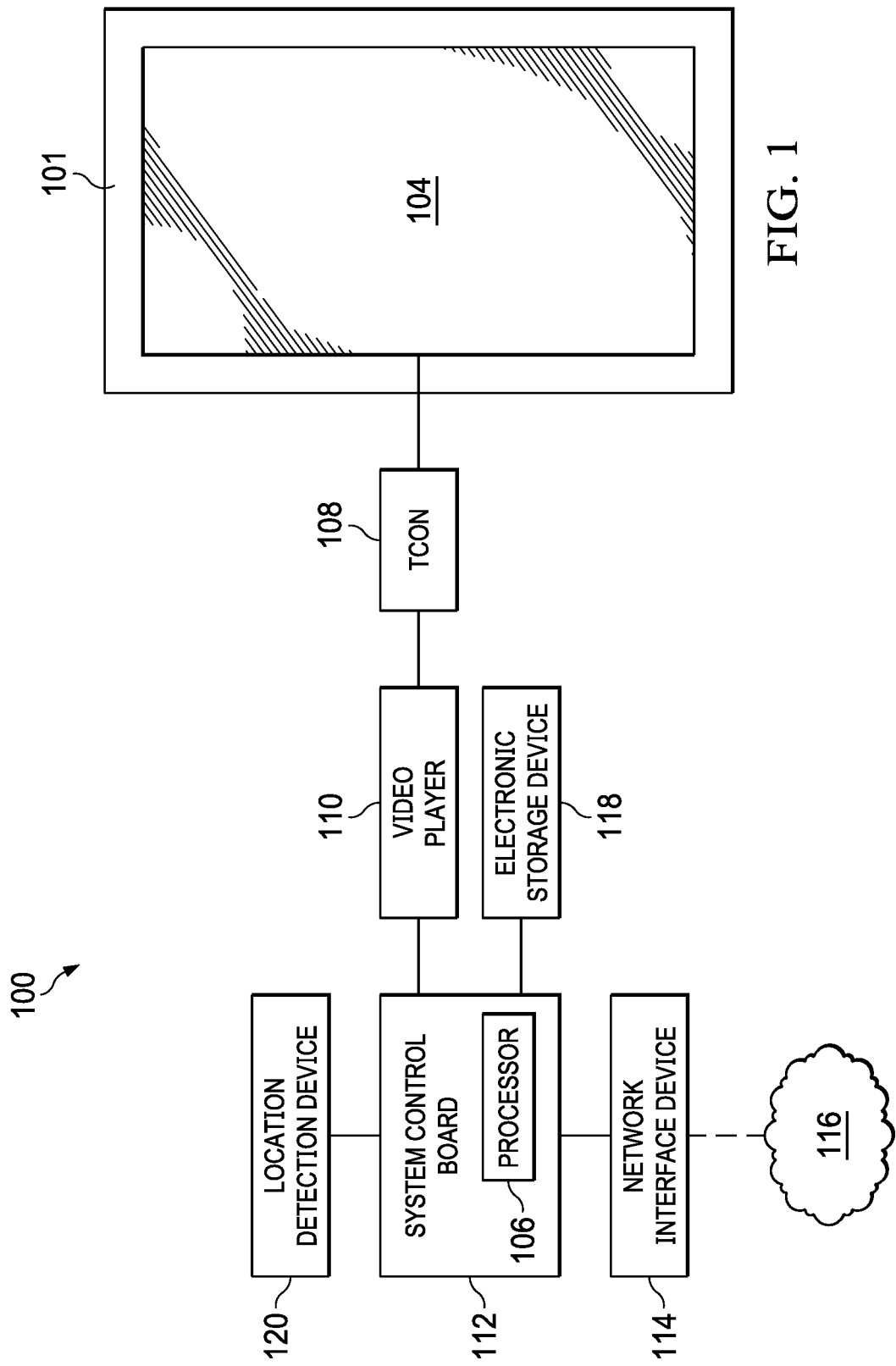
FIG. 1 is a simplified block diagram illustrating exemplary components of an exemplary display assembly.

FIG. 1 presents a simplified block diagram of an exemplary display assembly 100. The display assembly 100 may include a housing 101. The housing 101 may partially or completely surround an electronic display 104. The electronic display 104 may be any type of electronic display 104 such as, but not limited to, liquid crystal, plasma, light-emitting polymer, organic light emitting diode (OLED) displays, and the like. The housing 101 may be any size or shape. In exemplary embodiments, the housing 101 may define a cavity configured to house a variety of components described herein, including but not limited to the electronic display 104.

A timing and control board (TCON) 108 may be electrically connected to the electronic display 104. A video player 110 may be electrically connected to the TCON 108 and to a system control board 112. The video player 110 and TCON 108 may be configured to display still or video images on the electronic display 104, preferably as directed by the system control board 112. The images or videos may be stored on an electronic storage device 118. In some exemplary embodiments, the electronic storage device 118 may be local to the display assembly 100. In other exemplary embodiments, the electronic storage device 118 may be a networked device that is located remote from the display assembly 100.

The system control board 112 may be configured to provide display setting instructions for the electronic display 104. The display settings may include, for example and without limitation, what images are to be displayed, in what order the images are to be displayed, the length of time the images are to be displayed, and the like. The system control board 112 may additionally provide appearance setting instructions for the electronic display 104. The appearance settings may include, for example and without limitation, levels for brightness, color saturation, warmth, volume, contrast, and the like. The appearance and display settings may be pre-programmed or may be altered at any time, such as by a remote user.

The processor 106 may be in electrical connection with the system control board 112. The processor 106 may direct the system control board 112, or other components, to adjust the appearance settings of the electronic display 104. The system control board 112 may be electrically connected to a network interface device 114. The network interface device 114 may facilitate a connection with, and communication over, a communications network 116 such as, but not limited to, an intranet, the Internet, the world wide web, a cellular network, some combination thereof, or the like. This connection may permit a remote user to alter the appearance settings and display settings, and to monitor the performance and operation of, the display assembly 100.

The system control board 112 may additionally be electrically connected to a location detection device 120. In exemplary embodiments, the location detection device 120 may be a GPS-enabled device. In other exemplary embodiments, the location detection device 120 may operate by the use of multilateration, trilateration, etc., of radio tower signals, such as but not limited to, cellular network towers, Wi-Fi routers, and the like. Those having ordinary skill in the art will recognize any location detection method may be utilized. In other exemplary embodiments, the location of the display assembly 100 may be pre-programmed. The location of the display assembly 100 may be adjusted periodically by user input.

Figure 2:
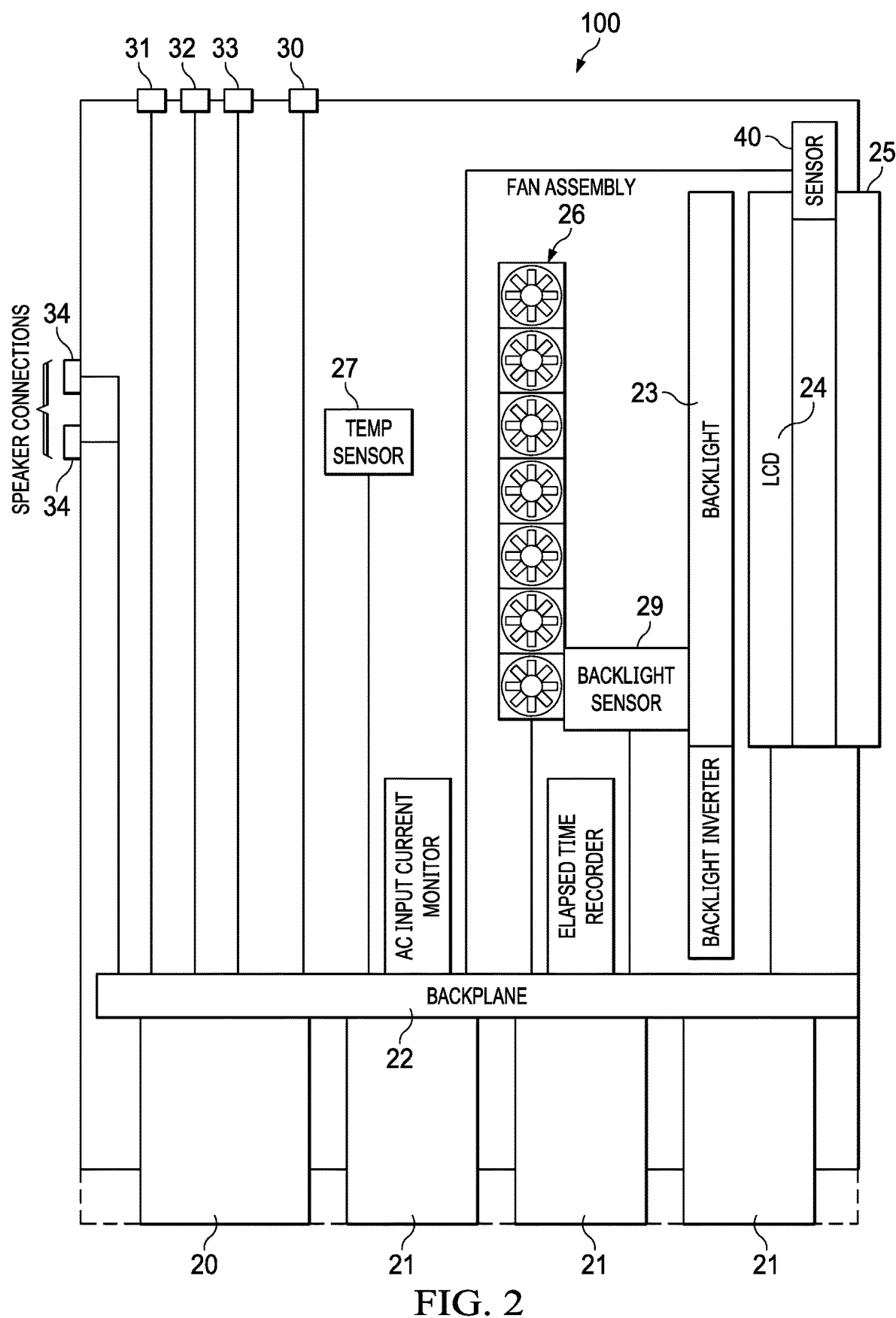
FIG. 2 is another simplified block diagram illustrating exemplary components of an exemplary display assembly.

FIG. 2 is a block diagram illustrating various components that may be used within the same or another exemplary embodiment of a display assembly 100. One or more power modules 21 may be electrically connected with a backplane 22. The backplane 22 may be provided as a printed circuit board and may be configured to facilitate electrical communication and/or power distribution between some or all components of the display assembly 100. A display controlling assembly 20 may also be electrically connected with the backplane 22. The display controlling assembly 20 preferably includes a number of different components, including but not limited to, the video player 110, electronic storage device 118, processor 106, and system control board 112 which are programmed to perform any of the logic that is described herein.

The display assembly 100 may comprise a backlight 23, display layer 24, and a front transparent display panel 25. The display layer 24 may be, for example without limitation, a liquid crystal layer. The backlight 23 may be, for example without limitation, a CCFL or light emitting diode (LED)

backlight, though any kind of illumination device is contemplated. It should be noted that although an LCD type display is illustrated, embodiments can be practiced with any type of electronic image-producing assembly. Thus, other flat panel displays could be used, such as, without limitation, plasma, light-emitting polymer, organic light emitting diode (OLED) displays, and the like. In embodiments where the display does not include a traditional backlight, such as but not limited to OLED type displays, then the term "backlight" can be replaced with "display" and the term "backlight level" can be replaced with "display level." A fan assembly 26 is also shown for optionally cooling components of the display assembly 100 that may reach elevated temperatures. While a single fan assembly 26 is illustrated, it is contemplated that any number of fan assemblies 26, each including any number of fans, may be utilized at any number of locations throughout the display assembly 100. One or more temperature sensors 27 may be used to monitor the temperature of the display assembly 100 and its various components, and selectively engage the fan assembly 26 when cooling is needed. In exemplary embodiments, one or more of the temperature sensors 27 may be located in close proximity to an intake point for ambient air to measure the temperature of ingested ambient air.

A variety of different electrical inputs/outputs are also shown, and all or only a select few of the inputs/outputs may be practiced with any given embodiment. As shown here, an AC power input 30 may deliver incoming power to the backplane 22. A video signal input 31 may be provided and may be configured to receive video signals from a plurality of different sources. In an exemplary embodiment, the video signal input 31 may be an HDMI input. Two data interface connections 32 and 33 are also shown to be a part of the exemplary display assembly 100. One of the data interface connections may be a RS2332 port or an IEEE 802.3 jack that can facilitate user setup and system monitoring. Either form of the connection may permit electrical communication with a personal computer. The other data interface connections may include a network connection such as an Ethernet port, wireless network connection, a satellite network connection, some combination thereof, or the like. This second data interface connection preferably allows the display assembly to communicate with the internet and may also permit a remote user to communicate with the display assembly 100. The second data interface connection may also provide video data through a network source, and may be utilized to transmit display settings, error messages, and various other forms of data to a website for access and control by the user. Optional audio connections 34 may also be provided for connection to internal or external speaker assemblies, microphones, or the like. It is not required that the data inputs 31, 32, and 33 receive their data through a wired connection, as many embodiments may utilize wireless networks or satellite networks to transmit data to the display assembly. The various types of wireless/satellite receivers and transmitters have not been specifically shown due to the large number of variable types and arrangements, but such receivers and transmitters would be well understood by a person of ordinary skill in the art.

A backlight sensor 29 may be placed within the backlight cavity of the display assembly 100 to measure the brightness level within the backlight cavity. Additionally, a display light sensor 40 may be positioned in front of the display layer 24 in order to measure the brightness level of the display layer 24. Either sensor 29, 40 can be used in a traditional feed-back loop, or otherwise, to evaluate the control signals being sent to the power modules 21 and the resulting backlight brightness intensity or display brightness intensity generated in response.

Information for monitoring the status of the various display components may be transmitted through either of the two data interface connections 32 and 33, so that the user can be notified when a component may be functioning improperly, about to fail, or has already failed and may require replacement. The information for monitoring the status of the display may include, but is not limited to: power supply status, power supply test results, AC input current, temperature sensor readings, fan speed, video input status, firmware revision, and light level sensor readings. Also, the user may adjust settings including, but not limited to: on/off, brightness level, various alert settings, IP address, customer defined text/video, display matrix settings, display of image settings via OSD, and various software functions. In some embodiments, these settings can be monitored and altered from either of the two data interface connections 32 and 33.

Figure 3:
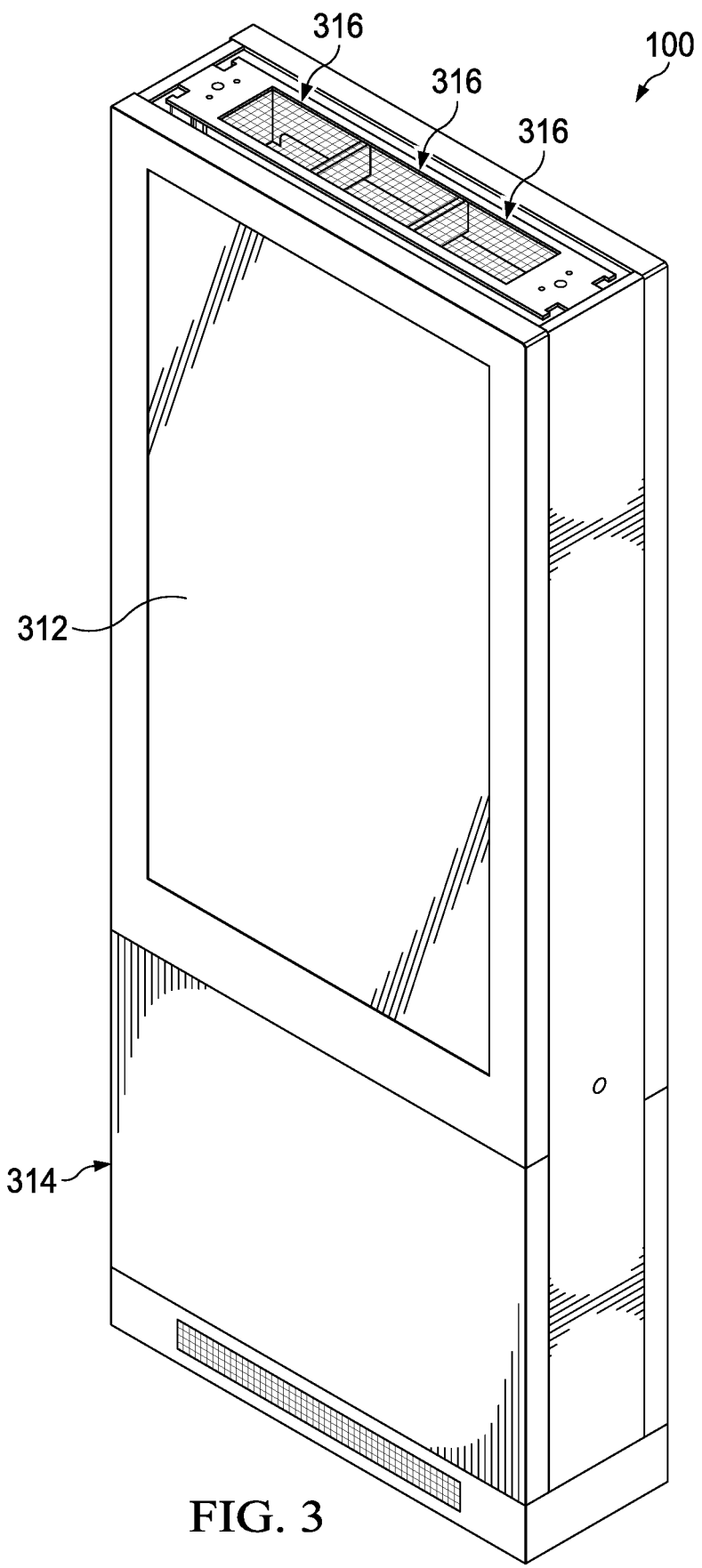
FIG. 3 is a perspective view of an exemplary display assembly.

FIG. 3 is a perspective view of another exemplary display assembly 100. The display assembly 100 may comprise one or more electronic display subassemblies 312 located on a housing 314. In exemplary embodiments, a first and second electronic display subassembly 312 may be mounted to the housing 314 in a hinged fashion such that the electronic display subassemblies 312 are capable of being rotated between a closed position, wherein the electronic display subassembly 312 is in contact with the housing 314, and an opened position wherein the electronic display subassembly 312 is located away from the housing 314. One or more openings 316 may be located on or around the housing 314 such that ambient air 328 may be ingested into, or exhausted from, the display assembly 100. The housing 314 may be configured to permit the display assembly 100 to be mounted to a sidewalk, the ground, a building, a bus shelter, a vehicle, a wall, a billboard, in a window, in a storefront, or the like.

Figure 4:
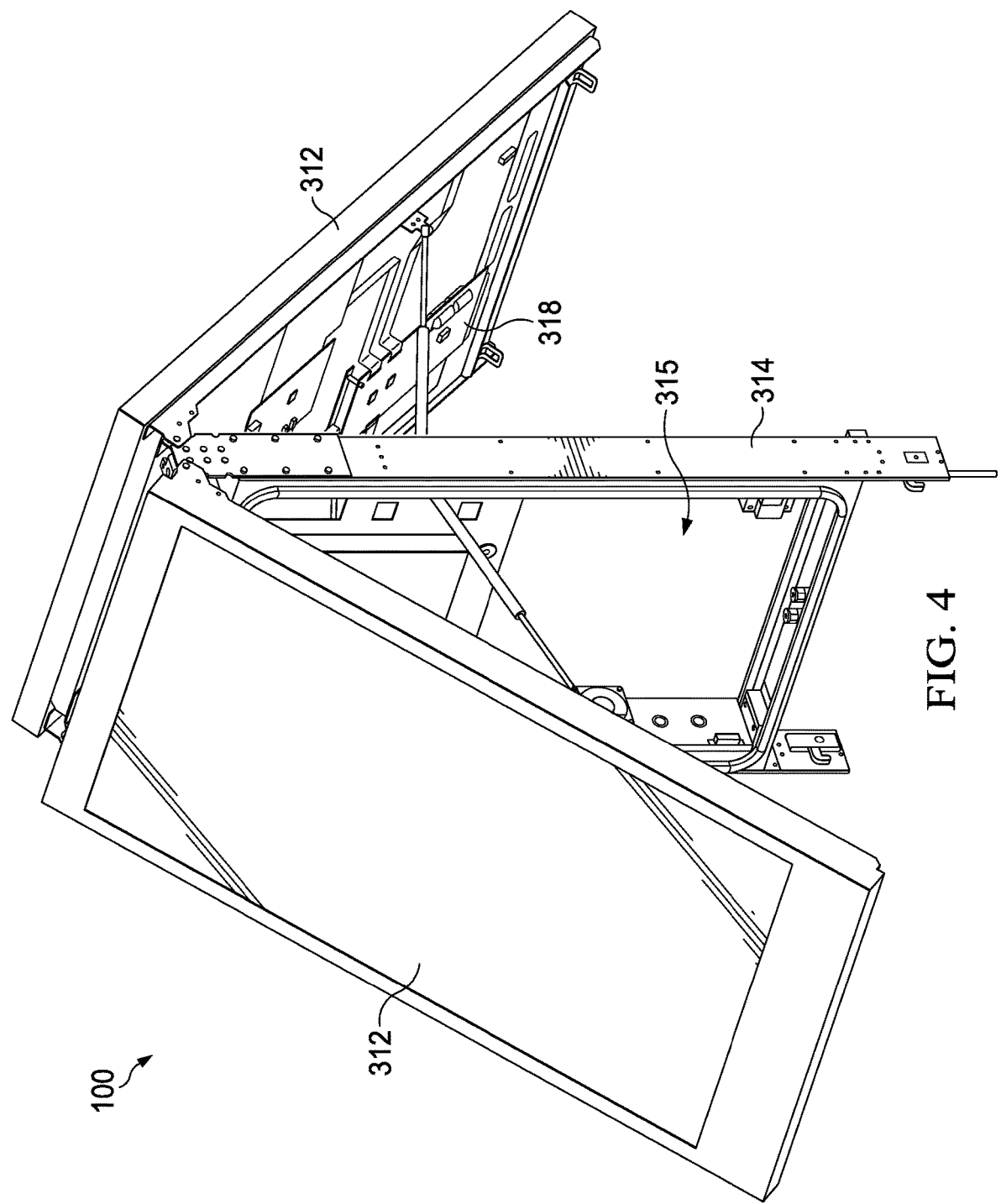
FIG. 4 is a perspective view of the exemplary display assembly of FIG. 3 with a first and second electronic display subassembly in an open position so as to illustrate additional components of the exemplary display assembly.

FIG. 4 is a perspective view of the assembly of FIG. 3 with a first and second electronic display subassembly 312 located in an open position so as to illustrate additional components of the display assembly 100. In exemplary embodiments, the rear surfaces of the two electronic display subassemblies 312 and the housing 314 may define a cavity 315 located therebetween. Assist devices may extend between the housing 314 and the electronic display subassemblies 312 to assist in moving the electronic display subassemblies 312 between the opened and closed positions. These assist devices may also assist in securing the electronic display subassemblies 312 in the opened or closed positions. The assist devices may be gas springs, gas struts, pullies, levels, ratcheting devices, struts, members, springs, counter weights, cams, some combination thereof, or the like.

Figure 5:
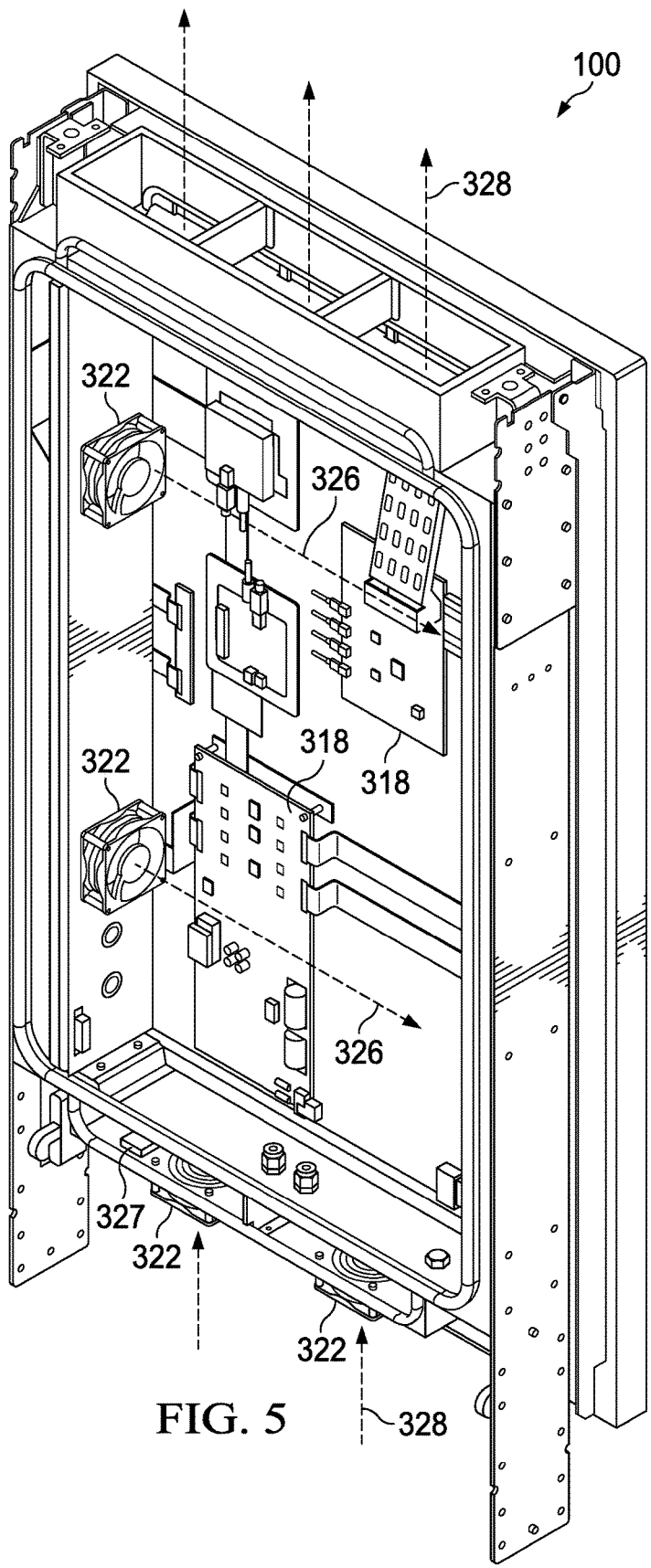
FIG. 5 is a perspective view of the exemplary display assembly of FIG. 3 with one of the electronic display subassemblies removed so as to illustrate exemplary air pathways of the exemplary display assembly.
Figure 6:
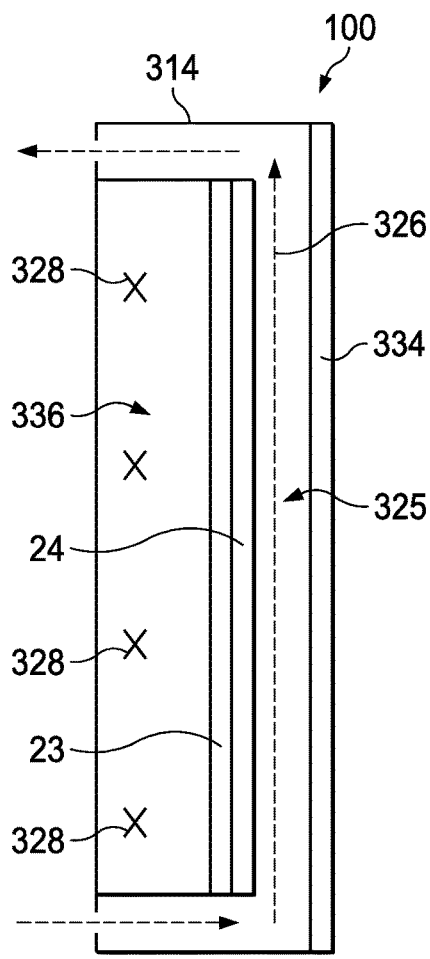
FIG. 6 is a top sectional view of one of the exemplary electronic display subassemblies of FIG. 3 which also illustrates exemplary air pathways.

FIG. 5 is a perspective view of the display assembly 100 of FIG. 3 with one of the electronic display subassemblies 312 removed so as to illustrate additional components of the display assembly 100. FIG. 6 is a top sectional view of one of the electronic display subassembly 312 of FIG. 3. FIGS. 5 and 6 illustrate an exemplary flow of ambient air 328 and circulating gas 326 through the display assembly 100. Ambient air 328 may enter from the ambient environment through the intake opening 316 and may pass through a channel 336 in one or more of the electronic display subassemblies 312. In exemplary embodiments, the channel 336 may be located such that ambient air 328 passes behind the backlight 23 for the display layer 24, though any location is contemplated. In other exemplary embodiments, the ambient air 328 may instead pass through the housing 314. In such embodiments, the circulating gas 326 may not be required.

The display layer 24 may be a liquid crystal display ("LCD"), Light Emitting Diode ("LED"), Organic LED ("OLED"), type display or the like. The backlight 23 may comprise one or more incandescent light bulbs, LEDs, OLEDs, or the like. In exemplary embodiments, the backlight 23 may comprise multiple light bulbs, LEDs, OLEDs, or the like, which may be arranged in an array on a sheet behind the display layer 24 in a direct-lit arrangement, or adjacent thereto in an edge-lit arrangement, such as but not limited to, along the edge of a light guide located behind the display layer 331. In exemplary embodiments, a cover 334 may be located in front of the display layer 331. The cover 334 may be a transparent sheet, such as but not limited to, a cover glass.

In some exemplary embodiments, the display layer 24 may be transparent or translucent. The housing 314 may be configured to locate the display layer 24 over the cavity 315, such as but not limited to, a cooler, vending machine, display case, or the like. In other exemplary embodiments, the cavity 315 may provide an area for storage of various components and other equipment.

Ambient air 328 may exit the display assembly 100 though the opening 316 where it may be returned to the ambient environment. The illustrated intake and exhaust points are merely exemplary. Any number and location of intake and exhaust openings are contemplated. This pathway for the ambient air 328 may define an open loop. The ambient air 328 may be moved by one or more fans 322 placed along or near the open loop. One or more filtration devices may likewise be placed along the open loop. While the ambient air 328 is illustrated as traveling vertically from bottom to top, it is contemplated that the ambient air 328 may also travel vertically from top to bottom. Alternatively, or in addition, the ambient air 328 may travel horizontally.

Circulating gas 326 may travel from the cavity 315 through one or more of the electronic display subassemblies 312. In exemplary embodiments, the circulating gas 326 may travel through a front channel 325 located between the cover 334 and the display layer 24. A similar pathway may be taken with a second flow of circulating gas 326 within the second, or any other additional electronic display subassemblies 312. Regardless, the circulating gas 326 may be returned to the cavity 315. This pathway(s) of the circulating gas 326 may define one or more closed loops. The circulating gas 326 may be moved by one or more fans 322 placed along the closed loops. While the circulating gas 326 is illustrated as traveling horizontally, it is contemplated that alternatively, or in addition, the circulating gas 326 may travel vertically. In exemplary embodiments, the open loop and the closed loops may be configured to substantially prevent the ambient air 328 and the circulating gas 326 from mixing. In particular, the closed loop may be substantially sealed to prevent particulate in the ambient air 328 from mixing with the circulating gas 326. Any number of display subassemblies 312 within a given housing 101 are contemplated.

The illustrated open loop and closed loops are merely exemplary and are not intended to be limiting. Any pathway for ambient air 328 is contemplated. Likewise, any pathway for circulating gas 326 is contemplated. It is contemplated that in some embodiments, the closed loops and circulating gas 326 may not be required. In still other exemplary embodiments, the circulating gas 326 and closed loops may be limited to traveling within the cavity 315.

Figure 7:
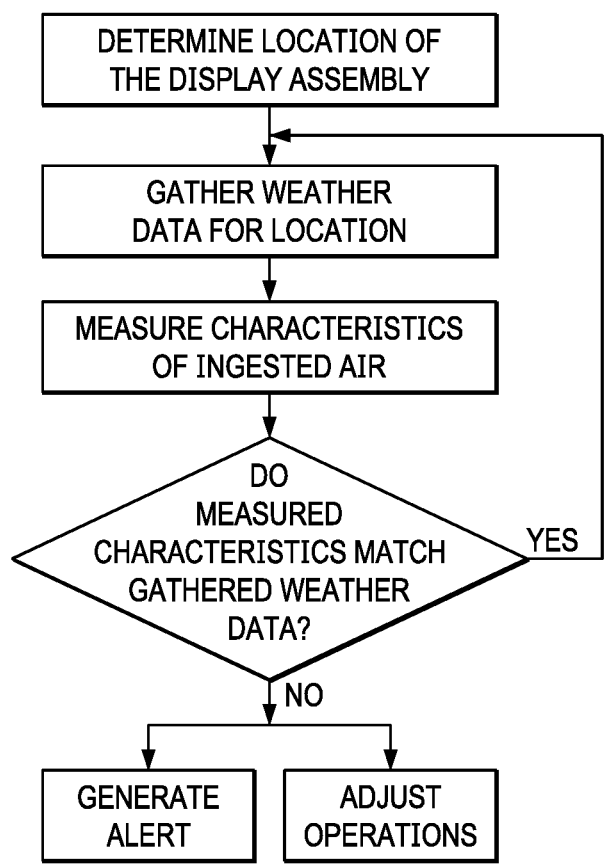
FIG. 7 is a flowchart of exemplary logic that may be used with the exemplary display assemblies.

FIG. 7 is a flowchart of exemplary logic that may be used with any of the aforementioned embodiments of the display assembly 100. The location of the display assembly 100 may be determined. In exemplary embodiments, the location may be determined by the location detection device 120. However, in other exemplary embodiments, the location may be preprogrammed and periodically updated by user input. Regardless, weather data for the location may be gathered. In exemplary embodiments, this weather data is gathered by retrieving weather data for the location from one or more web services, such as but not limited to openweathermap.org, by way of the communications network 116 and the network interface device 114. Such weather data may include, but is not limited to, temperature, air temperature, wind chill, high temperature, low temperature, average temperature, cloud cover, cloud height, chance of rain, chance of other precipitation, the presences of rain, snow, hail, or other precipitation, dew point, humidity, barometric pressure, mist, fog, precipitation intensity, precipitation amount, haze, dust, smoke, sand, volcanic ash, wind speed, wind direction, squalls, tornadoes, dust whirls, and the like. Such weather data may include present weather data, historical weather data, and predicted future weather conditions. The weather data may be stored on the electronic storage device 118.

The characteristics of the ingested ambient air 328 may be measured. Measurements may be made by way of one or more of the sensors 27, 327. The measured characteristics may include, but are not limited to, the temperature, moisture content, barometric pressure, speed, composition, and the like of the ingested ambient air 328. The data regarding characteristics of the ingested ambient air 328 may be stored on the electronic storage device 118. One or more additional sensors 27, 327 may likewise be located at or near the exhaust to measure the temperature of the exhausted ambient air 328. Any number of sensors 27, 327 at any number of locations configured to read any number of characteristics of the ambient air 328 are contemplated.

The electronic storage device 118 may comprise software instructions, which when executed configure the system control board 112 and/or the processor 106 to compare the weather data against the measured characteristics of the ingested ambient air 328. If the weather data matches the measured characteristics of the ingested ambient air 328, then the process may be repeated continuously, at any given interval, or on demand. In exemplary embodiments, after initially determining the location of the display assembly 100, the steps of gathering weather data and measuring characteristics of the ingested air may be repeated. Stated another way, the step of determining the location of the display assembly 100 may not necessary require repetition.

If the weather data does not match the measured characteristics of the ingested ambient air 328, then an alert may be generated. The alert may be displayed on the display assembly 100. Alternatively, or in addition, the alert may be transmitted to one or more remote devices by way of the network interface device 114 and the communications network 116. A margin of error may be utilized such that an alert is only generated when the difference between the weather data and the measured characteristics of the ingested ambient air 328 is beyond the margin of error.

The alert may be transmitted back to a remote user or remote network operations center 200. The alert may indicate re-ingestion of heated exhaust ambient air or an occlusion in the open loop pathway. Occlusions in the closed loop pathway are unlikely to be experienced as the closed loop pathway is generally, but not necessarily, substantially sealed from contaminants and debris which may otherwise be ingested into the open loop pathway.

Alternatively, or in addition, if the weather data does not match the measured characteristics of the ingested ambient air 328 the operations of the display assembly 100 may be adjusted. For example, without limitation, certain fans 26, 322 may be activated or the speed of such fans 26, 322 may be adjusted. This may cause the ambient air 328 to be exhausted further from the display assembly 100. Additionally, or alternatively, this may cause ambient air 328 from further away from the display assembly 100 to be ingested. Regardless, this may draw in cooler (or bring down the average temperature of) ambient air 328 relative to the recently exhausted ambient air 328. If the weather data does not match the measured characteristics of the ingested ambient air 328, an alert may be generated.

As a further example, again without limitation, the power levels for the backlight 23 may be adjusted in response to the alert. In exemplary embodiments, the backlight 23 may be decreased in order to reduce the amount of heat generated by the display assembly 100.

The display assembly 100 operational adjustments may be performed automatically or manually. In other exemplary embodiments, a technician may be dispatched to evaluate the display assembly 100. The dispatch of a technician may be initiated manually or automatically. For example, without limitation, the display assembly 100, or a remote network operations center 200, may automatically generate and transmit a request for service to a technician in proximity to the display assembly 100.

A margin of error may be utilized such that display operations are only adjusted when the difference between the weather data and the measured characteristics of the ingested ambient air 328 is beyond the margin of error. The margin of error for display operations may be the same or different from the margin of error for the alert generation. The process may be repeated continuously, or at any given interval.

The margin(s) of error may be determined, at least in part, by an analysis of historical data or by prediction. For example, without limitation, the inherent variations in weather conditions resulting from the distance between the location where the measurements were taken to generate the weather data and the location of the display assembly 100 may result in differences between the weather data and the measured characteristics of the ingested ambient air 328. As such, the margin(s) of error may be set to reflect historical or predicted instances where the difference was large enough to indicate a problem with re-ingested of exhausted ambient air 328 or occlusion in the open loop pathway(s). This may eliminate some or all instances where the difference was due to the distance between the point of measurement or other false alarms. As a further example, again without limitation, the margin(s) of error for one display assembly 100 may be determined by setting the same or a similar margin(s) of error for display assemblies 100 having similar distances between the location of the display assembly 100 and the location of the measurement point for the weather data.

For example, without limitation, the alert may indicate re-ingestion of exhausted ambient air 328 where the measured characteristics of the ingested ambient air 328 are higher than the temperature of the ambient air as provided in the gathered weather data by the margin of error. As a further example, without limitation, the alert may indicate an occlusion problem where the measured characteristics of the ingested ambient air 328 are changing at a rate outside the margin of error as compared to the changes in the temperature of the ambient air as provided in the gathered weather data.

As a further example, again without limitation, the update rate of the weather data and the measured characteristics of the ingested ambient air 328 may be different. The margin(s) of error may be higher or otherwise different during periods of temperature change, such as but not limited to, during sunrise or sunset, when weather fronts are passing, or the like. Similar to as described above, the margin(s) of error in such situations may be based on an analysis of historical data or predictions. In exemplary embodiments, the margin(s) of error may be selected to minimize or prevent the number of false alarms while capturing the all or most of the instances where the exhausted ambient air 328 is being re-ingested by the display assembly 100.

The historical information drawn upon may be from any one particular display assembly 100 and/or any number of the display assemblies 100. Alternatively, or additionally, the historical information drawn upon may be from historical weather data. Regardless, the analysis or prediction may be made manually or by use of an algorithm, machine learning program, or the like. The margin(s) or error may be applied across any number of the display assemblies 100.

It is notable that the differences between the measured characteristics and the gathered weather data may be based on data from a particular point in time. For example, without limitation, the measured characteristics of the ingested ambient air may be 70 degrees Fahrenheit and the gathered weather data may be 71 degrees Fahrenheit, which may be within a 2 degree Fahrenheit margin of error. In other exemplary embodiments, the differences between the measured characteristics and the gathered weather data may be based on a rate of change of data over a particular time period. For example, without limitation, the measured characteristics of the ingested ambient air may be a 2 degree Fahrenheit rise per hour and the gathered weather data may be 4 degrees Fahrenheit rise per hour, which may be outside of a 1 degree Fahrenheit per hour margin of error.

Figure 8:
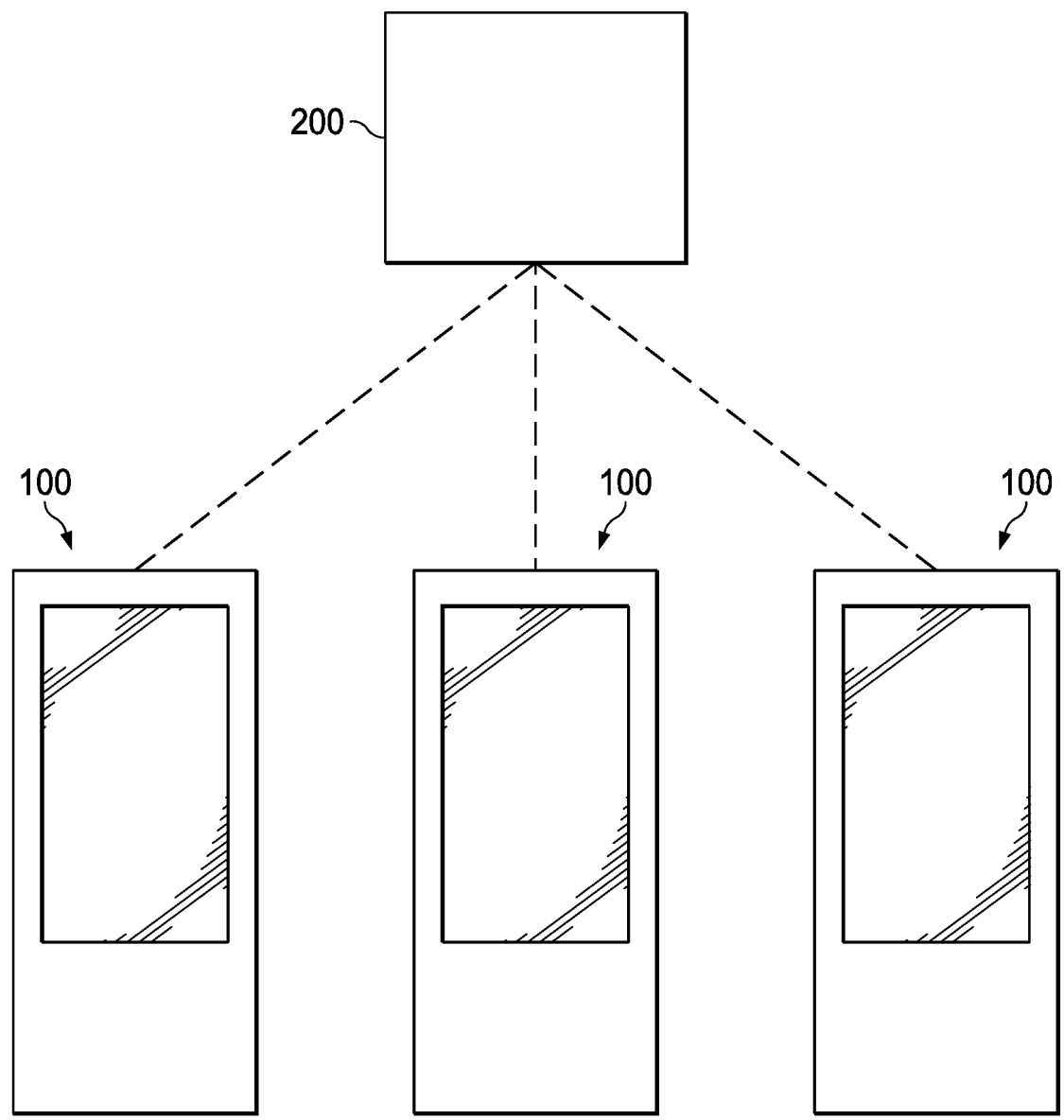
FIG. 8 is a plan view of an exemplary system.

FIG. 8 is a plan view of an exemplary system illustrating multiple display assemblies 100 in electronic communication with the network operations center 200. The network operations center 200 may be remote from one or more of the display assemblies 100. The network operations center 200 may comprise or more computers. In other exemplary embodiments, the network operations center 200 may be a personal electronic device for a remote user. In still other exemplary embodiments, the network operations center 200 may be in electronic communication with one or more remote customers by way of the customer's respective personal electronic devices.

Any embodiment of the present invention may include any of the optional or preferred features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

Certain operations described herein may be performed by one or more electronic devices. Each electronic device may comprise one or more processors, electronic storage devices, executable software instructions, and the like configured to perform the operations described herein. The electronic devices may be general purpose computers of specialized computing device. The electronic devices may be personal computers, smartphone, tablets, databases, servers, or the like. The electronic connections described herein may be accomplished by wired or wireless means.

What is claimed is:

1. A display assembly for detecting abnormal operating conditions, said display assembly comprising:
    a housing;
    an electronic display located within said housing;
    an airflow pathway through said housing;
    one or more fans placed along said airflow pathway and configured to ingest air into said airflow pathway, circulate said ingested air through at least a portion of said housing, and exhaust said ingested air when activated;
    one or more sensors for measuring characteristics of the ingested air in the airflow pathway;
    one or more processors in electronic communication with said one or more sensors; and
    one or more electronic storage devices in electronic communication with said one or more processors and comprising software instructions, which when executed, configure said one or more processors to:
        gather weather conditions for a location of the display assembly;
        receive measurements from the one or more sensors regarding characteristics of the ingested air;
        determine if the measurements are within a margin of error of expected measurements from the gathered weather conditions; and
        generate an alert if the measurements of the ingested air are not within the margin of error.

2. The display assembly of claim 1 wherein:
    said electronic display comprises a liquid crystal display; and
    said electronic display comprises a backlight provided in a direct backlighting arrangement for said liquid crystal display.

3. The display assembly of claim 2 wherein:
    said airflow pathway extends along a rear surface of the backlight.

4. The display assembly of claim 1 wherein:
    said abnormal operating conditions comprise gas recirculation or airflow occlusion.

5. The display assembly of claim 1 further comprising:
    an intake in said housing forming part of said airflow pathway; and
    an exhaust in said housing forming part of said airflow pathway.

6. The display assembly of claim 1 further comprising:
    a closed loop pathway through said housing configured to circulate circulating gas through at least a second portion of said housing.

7. The display assembly of claim 1 further comprising:
    a network interface device configured to place said one or more processors in electronic communication with a communications network.

8. The display assembly of claim 1 further comprising:
    a location detection device in electronic communication with said one or more processors and configured to determine the location of the display assembly.

9. The display assembly of claim 1 wherein:
    the one or more sensors are configured to measure at least the temperature of the ingested air; and
    the gathered weather conditions comprise ambient air temperature.

10. The display assembly of claim 9 wherein:
    said one or more electronic storage device comprises additional executable software instructions, which when executed, configure said one or more processors to determine said margin of error by analyzing historical differences between said gathered ambient air temperatures and said measured ambient air temperatures.

11. The display assembly of claim 1 wherein:
    said one or more electronic storage device comprises additional executable software instructions, which when executed, configure said one or more processors to determine a rate of change in the measurements of the ingested air and a rate of change of the gathered weather conditions; and
    said margin of error comprises a rate of change.

12. The display assembly of claim 1 wherein:
    the margin of error is relatively greater during sunrise and sunset hours; and
    the margin of error is relatively smaller during daytime and nighttime hours.

13. The display assembly of claim 1 wherein:
    said one or more electronic storage device comprises additional executable software instructions, which when executed, configure said one or more processors to decrease power supplied to a backlight of the electronic display upon determining that the measurements are outside of the margin of error.

14. The display assembly of claim 1 wherein:
    said one or more electronic storage device comprises additional executable software instructions, which when executed, configure said one or more processors to increase the speed of one or more fans upon determining that the measurements are outside of the margin of error.

15. The display assembly of claim 1 wherein:
    said one or more electronic storage device comprises additional executable software instructions, which when executed, configure said one or more processors to automatically generate a request service by a technician upon determining that the measurements are outside of the margin of error.

16. A method for detecting abnormal operating conditions in a display assembly, said method comprising the steps of:
    displaying one or more images at an electronic display within a housing;
    gathering, by way of a network interface device for the display assembly, weather conditions data for a location;
    ingesting ambient air into an open loop pathway, wherein said open loop pathway extends through a portion of said housing;
    measuring, by way of one or more sensors, characteristics of the ingested ambient air in the open loop pathway;
    determining that the characteristics of the ingested ambient air are not within a margin of error of expected measurements derived from the gathered weather conditions;
    generating an alert indicating said abnormal operating conditions; and
    transmitting, by way of the network interface device, said alert to at least one remote electronic device.

17. The method of claim 16 further comprising the steps of:
  generating a request for service of said display assembly; and
  transmitting, by way of the network interface device, said request for service to at least one other remote electronic device.

18. The method of claim 16 further comprising the steps of:
  decreasing a brightness level of a backlight for said electronic display; or
  increasing a speed level for one of more fans within said open loop pathway.

19. The method of claim 16 wherein:
  said characteristics comprise a temperature of the ambient air; and
  said abnormal operating conditions comprise gas recirculation or airway occlusion.

* * * * *